United States Patent
Seher et al.

(10) Patent No.: US 7,191,094 B2
(45) Date of Patent: Mar. 13, 2007

(54) SYSTEMS FOR APTITUDE TESTS FOR TESTING AN OBJECT FOR ITS INTENDED APPLICATION

(75) Inventors: Jens-Peter Seher, Stuttgart (DE); Gerhard Pross, Weil im Schönbuch (DE)

(73) Assignee: Koninklijke Philips Electronics, N.V., Eindhoven (NL)

( * ) Notice: Subject to any disclaimer, the term of this patent is extended or adjusted under 35 U.S.C. 154(b) by 142 days.

(21) Appl. No.: 10/517,457

(22) PCT Filed: Jun. 10, 2003

(86) PCT No.: PCT/IB03/02208

§ 371 (c)(1),
(2), (4) Date: Dec. 8, 2004

(87) PCT Pub. No.: WO03/107290

PCT Pub. Date: Dec. 24, 2003

(65) Prior Publication Data

US 2006/0009949 A1   Jan. 12, 2006

(30) Foreign Application Priority Data

Jun. 13, 2002   (DE) ............................... 102 26 212

(51) Int. Cl.
*G06F 19/00* (2006.01)

(52) U.S. Cl. ...................................... 702/182; 600/300

(58) Field of Classification Search ................ 702/182, 702/183–185, 188; 700/232, 237, 244; 705/2, 705/3, 28; 600/300, 573
See application file for complete search history.

(56) References Cited

U.S. PATENT DOCUMENTS

| 5,126,935 | A | 6/1992 | Saitou et al. |
| 5,489,414 | A | 2/1996 | Schreiber et al. |
| 5,989,917 | A | 11/1999 | McAleer et al. |
| 6,036,458 | A | 3/2000 | Cole et al. |
| 6,295,506 | B1 | 9/2001 | Heinonen et al. |
| 2004/0260204 | A1 * | 12/2004 | Boecker et al. ............. 600/584 |
| 2005/0110640 | A1 * | 5/2005 | Chung ..................... 340/572.1 |

* cited by examiner

*Primary Examiner*—Edward Raymond

(57) ABSTRACT

The present invention relates to an aptitude test system (4) which includes at least one object (1) which is provided with a data carrier (2) on which data associated with the object (1) is stored, as well as a test device (5) which includes a reading apparatus (6) whereby the data of the data carrier (2) can be transfer-red to a computer (7). The data includes aptitude data which characterizes at least one permissible application for the associated object (1). The computer (7) has access to current application data which characterizes a concrete application intended for the relevant object (1). For aptitude testing of the relevant object (1) the computer evaluates the aptitude data thereof and the actual application data. The computer (7) outputs a release signal when the object (1) is suitable for the intended application.

11 Claims, 1 Drawing Sheet

SYSTEMS FOR APTITUDE TESTS FOR TESTING AN OBJECT FOR ITS INTENDED APPLICATION

Figure 1:
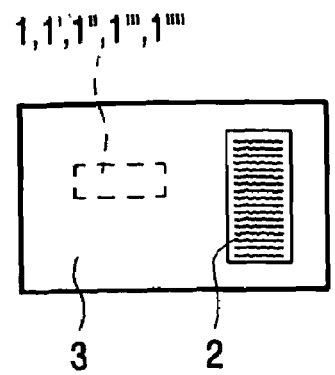

The present invention relates to an aptitude test system for testing an object in respect of its aptitude for an actual intended application.

In the field of so-called "point of care diagnosis" it is common practice to take a sample of a body fluid, for example, blood or urine, from a patient and to evaluate it already in the vicinity of the patient, for example, at the bedside, in the room, at the (intensive care) station or still in the hospital. The analysis of the fluid sample, and hence the diagnosis resulting therefrom, can thus be performed substantially faster than in the case of a customary procedure where the sample of the body fluid must first be sent to a central laboratory.

In particular so-called "cartridges" in which the relevant fluid sample is introduced are used for the point of care diagnosis. After the introduction of the body fluid, the cartridge is inserted into an analysis device in order to analyze the sample. Such cartridges contain inter alia chemicals which are required for the analysis of the relevant fluid sample. Such chemicals, which may also include calibration fluids, usually have a limited keeping quality only, because they are liable, for example, to disintegrate and/or dry out when stored too long. In order to enable the cartridges or their chemicals to be used for as long as possible, the cartridges customarily are individually packed in a packing (notably sealed therein) which is gastight and/or protects the cartridge against light, notably ultraviolet light. Such a packing is customarily provided with further information as regards the cartridge accommodated therein, for example, the type of cartridge as well as a date of expiry. Moreover, the packing may also be provided with a calibration code as well as a batch code. The indications given as regards the type of cartridge as well as the date of expiry constitute aptitude data characterizing the applications permissible for the associated cartridge.

In order to carry out a point of care diagnosis for which such a cartridge is used, the applicator or user, that is, notably a nurse, must check, already before opening the packing, whether the correct type of cartridge is concerned and whether the date of expiry has already been passed. If this check is forgotten or not performed correctly, the diagnosis device, in which the cartridge is inserted for the analysis of the sample contained therein, will recognize the error only after time-consuming calibration. Thus, on the one hand a loss of time is incurred and on the other hand the fluid sample taken may thus become unusable, so that the patient must be burdened again in order to take a further a fluid sample.

The checking of the date of expiry could easily be incorrectly performed or omitted because of the pressures of time often occurring in nursing, so that further time delays may be incurred.

It is an object of the present invention to provide an aptitude test system which simplifies the testing of an object for its aptitude for an actual intended application.

This object is achieved in accordance with the invention in the manner disclosed in the independent claim. Advantageous embodiments are disclosed in the dependent claims.

The invention is based on the general idea to provide, notably in the course of its manufacture, the object to be tested with a data carrier on which the aptitude data is stored in a machine-readable form, said data characterizing one or more permissible applications for the associated object. The proposed aptitude test system also includes a test device with a reading Apparatus which is constructed in such a manner that it can transfer the data from the data carrier to a computer which is suitably coupled to the reading apparatus. The computer in its turn has access to actual application data which characterizes an actual or concrete application for the relevant object. The computer can then perform an aptitude test on the relevant object by comparing the aptitude data thereof with the actual application data. Should the computer in the course of this aptitude test determine that the actual tested object is suitable for the intended concrete application, the computer can output an appropriate release signal. Alternatively, or additionally, the computer can output an appropriate alarm signal when the aptitude test reveals that the relevant object is not suitable for the actual intended application. The use of machine-readable data on the object as well as a suitable reading apparatus enables transfer errors as well as errors occurring during the evaluation of the data to be minimized. The reliability that the released object is indeed suitable for the actual intended application is enhanced by means of the aptitude test system in accordance with the invention.

As regards the previously mentioned example concerning the point of care diagnosis, the foregoing means that the cartridge, or the packing thereof, is provided with the data carrier which contains at least the date of expiry of the cartridge or its chemicals as aptitude data. The computer of the test device knows the current date and can thus simply determine whether the use of the tested cartridge is still permissible. Depending on the aptitude test, the computer can then trigger, for example, the emission of a green or a red light signal which can be readily identified by the relevant user.

In an advantageous further embodiment, the test device may be coupled to a processing device which processes the relevant object in dependence on the result of the aptitude test. This step enables expensive and/or time-consuming processing of the object to be avoided when the aptitude test reveals that the relevant object is not suitable for the actual intended application. This processing device may in principle be constructed in an arbitrary manner and carry out an arbitrary processing of the object, be it that such processing should not be the intended application.

In a preferred further embodiment said processing device is constructed to open a packing in which the object to be tested is packed. If the result of the aptitude test is positive, the computer instructs the processing device to open the packing. If the result of the aptitude test is negative, the packing is not opened. Consequently, the user directly recognizes whether the tested object is suitable for the intended use or not. The processing device may also be constructed, for example, in such a manner that it feeds the unusable objects in a closed packing still to an appropriate storage container.

When this embodiment is used for the described example, the user feeds the cartridge still packed in its packing to the processing device. Prior to the opening of the packing, the aptitude of the cartridge is tested therein, that is, notably its date of expiry. In as far as the use of this cartridge is still permissible, its packing is automatically opened, and otherwise it is not. The user can thus remove exclusively a permissible cartridge from its packing. In this embodiment the testing of the aptitude data, notably the date of expiry, can no longer be forgotten prior to the use of the cartridge, that is, in as far as the opening of the packing is performed exclusively by means of the processing device.

Even though the testing of cartridges intended for point of care diagnosis concerns a preferred application of the aptitude test system in accordance with the invention, all kinds of other objects can in principle be tested for aptitude by means of a correspondingly constructed test device. Notably in the medical field there are important further applications, one of which will be described by way of example hereinafter. The object to be tested may be a medicament or a combination of medicaments. This medicament or combination of medicaments is suitable for patients with a given clinical picture and notably have a given physical constitution. The associated aptitude data include above all identification data enabling identification of the medicament or the combination of medicaments. Moreover, the aptitude data may again include a date of expiry. The data carrier may be provided, for example, on a packing of the medicament or the combination of medicaments. Before this medicament or combination of medicaments is administered to a given patient, the aptitude test is performed; for this test the computer knows the patient data of the actual patient which is necessary for the medication of this patient. For example, such patient data includes an indication that the relevant patient may be administered only a given medicament or only a given combination of medicaments. Additionally, or alternatively, the patient data may also include information enabling the computer to test, on the basis of the clinical picture and notably the physical constitution of the relevant patient, whether the intended medication is suitable for this patient. The patient data may also include a medication timetable on the basis of which the computer can determine whether the intended medication is permissible or not at the current instant. Additionally, the date of expiry of the intended medication can also be tested. In this embodiment incorrect medication can better be avoided. The protection against incorrect medication can be additionally improved in particular in conjunction with a processing device which is suitable for opening a packing; the packing of the medicament or the combination of medicaments is then opened exclusively if the computer instructs the processing device to open the packing after a positive aptitude test.

In addition to the foregoing examples from the medical field, the aptitude test system in accordance with the invention can also be used in other fields. A further embodiment will be described hereinafter by way of example. In conformity with an advantageous embodiment, the test device may be a cash register or be integrated in such a register. The objects are then consumer products provided with a date of expiry, until which appropriate use of the object is to be ensured. The objects are notably items of food which should be consumed before the date of expiry. The aptitude data of such objects then includes at least the date of expiry associated with the relevant object. Modern cash registers operate with an optical reading apparatus which reads the data provided on the relevant articles, usually being an article number. On the basis of the article number a computer of the cash register can associate an article description as well as the price of the article with the article. In accordance with the invention it is proposed to add the date of expiry to the data associated with the article, so that upon reading the date of expiry can also be read so as to compare it with the current date. When this aptitude test reveals that the date of expiry of the relevant article has already been passed, the computer generates the alarm signal which initiates, for example, in the test device or the cash register, the output of an optical and/or acoustic alarm. The customer can then be informed that the date of expiry has passed and the customer can then decide whether or not to purchase the article nevertheless.

Additionally, or alternatively, a reduced price could be automatically assigned to the relevant article if the date of expiry date has been passed. The resultant enhanced comfort and advantages for the user as well as the advantages in respect of customer friendliness for the warehouses will be evident.

Further important features and advantages of the invention will become apparent from the dependent claims, the drawings and the description given with reference to the drawings.

It is to be understood that the features mentioned above and clarified hereinafter can be used not only in the respective stated combinations, but also in other combinations or individually, without departing from the scope of the present invention.

Preferred embodiments of the invention are shown in the drawings and will be elucidated in the following description in which identical references relate to identical or functionally identical or similar components.

IN THE DRAWINGS

Figure 2:
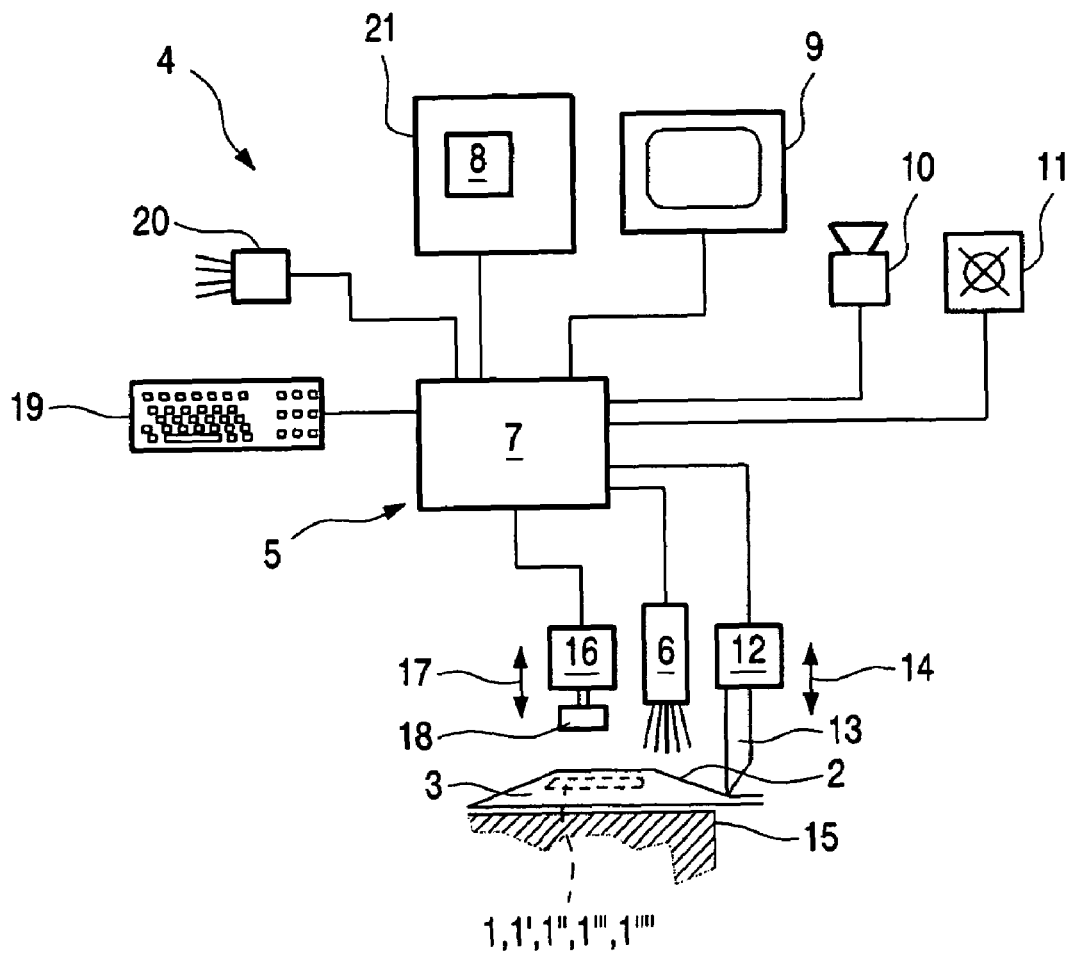

FIG. 1 is a plan view of an object in a packing provided with a data carrier, and FIG. 2 is a circuit diagram of an aptitude test system in accordance with the invention.

As is shown in FIG. 1, an object 1 which is denoted by a dashed line is provided with a data carrier 2 which is in this case provided on a packing 3 in which the object 1 is packed. In another embodiment the data carrier 2 may also be provided directly on the object 1, for example, when the data carrier 2 can be read through the packing 3 or when there is no packing 3. The data carrier 2 is a one-dimensional bar code in the present embodiment. The data carrier 2 may also be formed by a two-dimensional bar code. Furthermore, in principle any other data carrier 2 is feasible, notably magnetic, electronic and optical data memories.

The object 1 may in principle be an arbitrary object. In the described preferred embodiment the object 1 is assumed to be, by way of example, a cartridge 1' which can be used for the analysis of a body fluid sample in the context of a point of care diagnosis of a patient. Analogously, the following description also holds for an object 1 which is formed by a medicament 1" or by a combination of medicaments 1'''.

The data carrier 2 contains aptitude data which is associated with the object 1. This aptitude data characterizes one or more permissible uses for the associated object 1. In as far as the object 1 concerns a cartridge 1', the aptitude data includes at least a date of expiry until which the use of the cartridge 1' is permissible. Furthermore, the aptitude data may also enable identification of the relevant type of cartridge. In as far as the object 1 concerns a medicament 1" or a combination of medicaments 1''', the aptitude data advantageously includes identification data which enables identification of the medicament 1" or the combination of medicaments 1'''. Moreover, the aptitude data may also include a date of expiry for the medicament 1" or the combination of medicaments 1'''.

In conformity with FIG. 2, an aptitude test system 4 in accordance with the invention includes not only an object 1 of this kind which is provided with a data carrier 2, but also a test device 5. The test device 5 includes a reading apparatus 6 which is coupled to a computer 7. The reading apparatus 6 is constructed in such a manner that it can read the aptitude data stored on the data carrier 2 so as to apply it to the computer 7. The reading apparatus 6 in the embodiment shown herein is an optical bar code reading apparatus 6. It will be evident that in principle arbitrary other suitable reading apparatus 6 can be used in dependence on the data carrier 2 used.

The computer 7 has access to actual application data which is stored, for example, in an appropriate data memory 8. This actual application data characterizes a concrete application for which the actual object 1 being tested is intended. For example, the application data includes the current date. The computer 7 performs an aptitude test by evaluating the aptitude data of the concrete object 1 and the actual application data. For example, the computer 7 compares the date of expiry associated with the object 1 with the current date. The computer 7 generates a release signal when the object 1 is suitable for the intended application. Alternatively, or additionally, the computer 7 generates an alarm signal when the object 1 is not suitable for the intended application.

A plurality of output units, that is, a display screen 9, an acoustic signal generator 10 and an optical signal generator 11, are connected to the computer 7 in the embodiment shown herein. The result of the relevant aptitude test can be output by the computer 7 via at least one of these output units 9, 10, 11. For example, in the case of a positive result of the aptitude test, the optical signal generator 11 can emit a green light which informs the relevant user of the test device 5 that the object 1 is suitable for the intended application. In the case of a negative result of the aptitude test, the optical signal generator 11 can advantageously emit a red light signal. Furthermore, the acoustic signal generator 10 can output a suitable alarm tone; for example, the reason why the result of the aptitude test is negative can be displayed on the display screen 9.

A preferred embodiment of the aptitude test system 4 also includes a processing device 12 which enables automatic processing of the object 1 subsequent to the aptitude test. The processing device 12 in the embodiment shown herein is an opening device, that is, a processing device 12 which is arranged to open the packing 3. To this end, the processing device 12 includes a blade 13 which can be displaced relative to its cutting edge 15 in conformity with a double arrow 14, the relevant drive, however, not being shown herein. This processing device 12 is coupled to the test device 5 or to the computer 7 thereof. The computer 7 can thus control the processing device 12 in dependence on the aptitude test. If the result of the aptitude test is positive, the processing device 12 is controlled so as to open the packing 3. However, if the test result is negative, the processing device 12 is not driven so that the packing 3 remains closed. Instead, for example, there may be activated an invalidation device 16 which is provided with a stamp 18 which is adjustable in conformity with a double arrow 17 and whereby the object 1 or its packing 3 can be provided with a text indicating, for example, the invalidation of the object 1. To this end, the invalidation device 16 is coupled to the test device 5 or to the computer 7 thereof.

The test device 5 or its computer 7, moreover, may be coupled to input units, for example, a keyboard 19 and/or another reading apparatus 20. For example, a patient identification code can be input into the computer 7 via such input units 19, 20, which code enables the computer 7 to fetch patient data which may form part of the application data from a database 21 coupled thereto.

The aptitude test system 4 in accordance with the invention operates as follows:

First Embodiment

The first embodiment to be described in detail hereinafter involves an object 1 which is formed by a cartridge 1' which is to be used in the context of a point of care patient diagnosis. The cartridge 1' is still present in its packing 3 for better positioning. In order to enable the cartridge 1' to be used for receiving a body fluid sample, it is necessary to open the packing 3. To this end, the user inserts the packing 3 into the processing device 12 so as to start an automatic opening procedure. Prior to the opening procedure the computer 7 reads the aptitude data stored on the data carrier 2 and carries out the aptitude test in conjunction with the available application data. In the present case the computer 7 checks whether the date of expiry of the cartridge 1' has already been passed or not. Furthermore, the user can enter further application data, for example, the type of diagnosis and/or the patient identification code of the relevant patient, via one of the input units 19, 20. On the basis of the aptitude data, the computer 7 can then also check whether the cartridge 1' being tested is suitable for the intended diagnosis or for the intended patient. The computer 7 activates the processing device 12 to open the packing 3 only in the case of a positive result of the aptitude test. The relevant user then unambiguously recognizes whether the relevant cartridge 1' is suitable for the intended application or not. Furthermore, the user cannot omit this test, because the packing 3 is opened so as to remove the cartridge 1' therefrom only after a positive test result.

Second Embodiment

In the case where the object 1 is a medicament 1" or a combination of medicaments 1''', it is also advantageous to accommodate the medicament 1" or the combination of medicaments 1''' in a packing 3, for example, in an envelope which is provided with the data carrier 2. In this embodiment the user again opens the packing 3 by means of the processing device 12 by introducing the packing 3 therein. Prior to the opening of the packing 3, the computer 7 has to receive the patient identification code via one of the input units 19, 20. Using this patient identification code, the computer 7 can fetch from the database 21 the patient data necessary for the medication of the selected patient. Furthermore, via the reading apparatus 6, the computer 7 reads the aptitude data of the medicament 1" or the combination of medicaments 1''', said aptitude data containing the identification data for the identification of the medicament 1" or the combination of medicaments 1''' in the present case. The computer 7 can then determine whether or not the intended medication is suitable for the selected patient by comparing the aptitude data with the application data. The aptitude test then includes notably the testing whether interactions could occur with other medicaments already taken by the relevant patient. Furthermore, it can be tested whether the medication takes place at the prescribed instant. Finally, the date of expiry of the relevant medicament 1" or the combination of medicaments 1''' can be tested.

The computer 7 activates the processing device 12 so as to open the packing 3 only after it has been ensured that the tested medicament 1" or the tested combination of medicaments 1''' is suitable for the selected patient or is to be taken by the selected patient. The user thus unambiguously recognizes once more whether or not the selected medicaments 1", 1''' may be administered to the patient.

Third Embodiment

Whereas in the foregoing a description has been given of applications from the medical field, a completely different type of application will be described hereinafter. For example, the object 1 may be an item of food 1'''' which is contained in a packing 3 and with which there is also associated a data carrier 3. The data carrier 2 contains an article number associated with the item of food 1'''' as well as a date of expiry.

The test device 5 is integrated in a cash register (not shown) or forms a part of such a cash register. Hereinafter this cash register will also be denoted by the reference numeral 5. The cash register 5 reads, via the reading apparatus 6, the data stored on the data carrier 2 in order to apply it to the computer 7. In addition to the article number, aptitude data, in this case in the form of the date of expiry, is thus also transferred. Via a suitable clock the computer 7 knows the current date and can compare it with the supplied date of expiry of the item of food 1'''' in order to carry out the aptitude test. The aptitude test is negative at least when the date of expiry of the item of food 1'''' has already been passed. The cash register 5 then provides a corresponding alarm to the user. In a further embodiment it may additionally be arranged that such an alarm is provided already when a minimum period of keeping quality, commencing at the current date and guaranteed by the seller, can no longer be realized at the date of sale.

LIST OF REFERENCES 1 object
2 data carrier
3 packing
4 aptitude test system
5 test device
6 reading apparatus
7 computer
8 data memory
9 display screen
10 acoustic signal generator
11 optical signal generator
12 processing device
13 blade
14 double arrow
15 cutting edge
16 invalidation device
17 double arrow
18 stamp
19 keyboard
20 reading apparatus
21 database

The invention claimed is:

1. An aptitude test system which is suitable for testing an object (1) in respect of its aptitude for an actual intended application, which system includes:
   at least one object (1) which is provided with a data carrier (2) on which data associated with the object (1) is stored, and
   a test device (5) which includes a reading apparatus (6) whereby the data of the data carrier (2) can be transferred to a computer (7) which is coupled to the reading apparatus (6),
   the data being or including aptitude data which characterizes one or more permissible applications for the associated object (1),
   the computer (7) having access to actual application data which characterizes a concrete application envisaged for the relevant object (1),
   the computer (7) evaluating the aptitude data of the relevant object (1) and the current application data for the aptitude testing of the relevant object and outputting a release signal when the object (1) is suitable for the intended application and/or an alarm signal when the object (1) is not suitable for the intended application, characterized in that the aptitude data includes a date of expiry of the object (1) and the application data includes the current date, the computer (7) generating the alarm signal when the date of expiry of the object (1) has been passed when the aptitude test is carried out.

2. An aptitude test system as claimed in claim 1, characterized in that the test device (5) is coupled to a processing device (12) which processes the relevant object (1), or a packing (3) of the object (1), in dependence on the result of the aptitude test.

3. An aptitude test system which is suitable for testing an object (1) in respect of its aptitude for an actual intended application, which system includes:
   at least one object (1) which provided with a data carrier (2) on which data associated with the object (1) is stored, and
   a test device (5) which includes a reading aparatus (6) whereby the data of the data carrier (2) can be transferred to a computer (7) which is coupled to the reading aparatus (6),
   the data being or including aptitude data which characterizes one or more permissible applications for the associated object (1),
   the computer (7) having access to actual application data which characterizes a concrete application envisaged for the relevant object (1),
   the computer (7) evaluating the aptitude data of the relevant object (1) and the current application data for the attitude testing of the relevant object and outputting a release signal when the object (1) is suitable for the intended application and/or an alarm signal when the object (1) is not suitable for the intended application, characterized in that the test device (5) is coupled to a processing device (12) which processes the relevant object (1), or a packing (3) of the object (1), in dependence on the result of the aptitude test, characterized in that the object (1) includes a packing (3), that the processing device (12) is arranged to open the packing (3), and that the processing device (12) opens the packing (3) only when the computer (7) outputs the release signal.

4. An aptitude test system as claimed in claim 2 or 3, characterized in that the processing device (12) invalidates and/or marks the object (1) or its packing (3) when the computer (7) outputs the alarm signal.

5. An aptitude test, system as claimed in claim 1 or 3, characterized in that the test device (5) and/or the processing device (12) include an output unit (9, 10, 11) which provides the user of the test device (5) with an optical and/or acoustic indication of the result of the aptitude test.

6. An aptitude test system as claimed in claim 1 or 3, characterized in that the data carrier (2) is formed by a one-dimensional or two-dimensional bar code and that the reading apparatus (6) is formed by an optical bar code reading apparatus (6).

7. An aptitude test system as claimed in claim 3, characterized in that the aptitude data includes a date of expiry of the object (1) and that the application data includes the current date, the computer (7) generating the alarm signal when the date of expiry of the object (1) has been passed when the aptitude test is carried out.

8. An aptitude test system as claimed in claim 1 or 3, characterized in that
   the object (1) is a medicament (1'') and/or a combination of medicaments (1'''), the aptitude data includes a date of expiry of the medicament (1") or the combination of medicaments (1''') and/or identification data enabling identification of the medicament (1") or the combination of medicaments (1'''), the application data includes the current date and/or the current time and/or patient data required for medication of a patient so as to administer the medicament (1") and/or the combination of medicaments (1''') to a concrete patient, the computer (7) generates the alarm signal when the medicament (1") or the combination of medicaments (1''') is not suitable for administration to the intended patient.

9. An aptitude test system as claimed in claim 8, characterized in that the computer (7) has access to a database (21) in which the patient data of a plurality of patients is stored, and that the computer (7) can receive, via an input unit (19, 20) or the reading apparatus (6), a patient identification code of the actual patient intended to be administered the medicament (1") or the combination of medicaments (1'''), said patient identification code enabling the computer (7) to access the patient data of the relevant patient in the database (21).

10. An aptitude test system as claimed in claim 1 or 3, characterized in that the object (1) is a cartridge (1') intended for carrying out point of care diagnosis of a body fluid sample taken from a patient.

11. An aptitude test system as claimed in claim 1 or 3, characterized in that the test device (5) is a cash register or is integrated in such a cash register, the aptitude data is formed by a date of expiry associated with the relevant object (1) or contains this date of expiry, the application data is formed by the current date or by a given minimum period of keeping quality which commences at the current date, or includes the current date or said minimum period of keeping quality, the computer (7) generates the alarm signal when the date of expiry has been passed and/or when it is about to pass and/or when it will be passed within the minimum period of keeping quality.

* * * * *